United States Patent [19]
Walker

[11] 3,976,072

[45] Aug. 24, 1976

[54] BLINK-OPERATED EXTRACORPOREAL TEAR DUCT

[75] Inventor: Elijah C. Walker, Bethesda, Md.

[73] Assignee: The United States of America as represented by the Secretary of the Department of Health, Education and Welfare, Washington, D.C.

[22] Filed: Sept. 3, 1975

[21] Appl. No.: 609,985

[52] U.S. Cl. .............................. 128/260; 128/249; 351/158
[51] Int. Cl.² ........................................ A61M 31/00
[58] Field of Search .................... 128/260, 249, 248; 351/158

[56] References Cited
UNITED STATES PATENTS 3,826,258  7/1974  Abraham ........................... 128/260

OTHER PUBLICATIONS

"Keratoconjunctivitis Sicca & New Techniques in Its Management," *Medical Journal of Australia*, vol. 1, No. 2, Jan. 14, 1967, pp. 33–44.

"Mobile Infusion Pumps for Continuous Delivery . . . to Eye," Dohlman et al., *Annals of Opthalmogy*, Feb. 1971, pp. 126–128.

"A New Extracorporeal Tear Duct," G. D. Summers, —24th ACEMB, Oct. 31–Nov. 4, 1971, vol. 13, p.

*Primary Examiner*—Aldrich F. Medbery
*Attorney, Agent, or Firm*—Browdy and Neimark

[57] ABSTRACT

A blink-activated duct for supplying a solution to the eye of the user has a particular utility in introducing an artificial tear solution to the eye of those persons who are incapable of producing such a solution themselves. The duct consists of a reservoir section which contains the solution, and a pump section consisting of a contact lens or a Silastic tube assembly for delivering the solution directly to the eye. This pump section is activated by the eyelid compressing the contact lens or the Silastic tube assembly, causing the solution to be displaced to the eye and successively drawing additional solution from the reservoir section to the pump section due to the creation of a temporary vacuum.

8 Claims, 6 Drawing Figures

BLINK-OPERATED EXTRACORPOREAL TEAR DUCT

FIELD OF THE INVENTION

This invention relates to an apparatus for introducing a solution to the eye utilizing the blinking of the eye to activate the apparatus. This apparatus has particular utility in introducing an artificial tear solution to the eye.

BACKGROUND OF THE INVENTION

In order to function properly, the human eye must be constantly cleaned and bathed with a saline solution to eliminate dirt, dust or other irritants from the surface of the eye. Most humans have this saline solution automatically introduced to the eye by means of a tear duct. This duct is activated by the blinking action of the eye which in turn is actuated by the brain sensing certain irritants on the surface of the eye. Unfortunately, many people are incapable of producing their own tears and therefore this saline solution must be introduced to the eye by other means.

The prior art shows that several systems such as a gravity feed system and a mobile infusion system have been developed for dealing with this problem. While these systems do introduce artificial tears to the eye, they are not without their drawbacks. The gravity feed system is described by Flynn and Schulmeister in "Keratoconjunctivitis Sicca and New Techniques in its Management", Medical Journal of Australia, 1:34, 1967. In this system, artificial tears are supplied to the eye from a reservoir attached to the frame of a pair of eyeglasses. With the aid of gravity, the fluid flows from the reservoir through a series of tubes and into the inner corner of the eye. The main fault of this system, which the present invention overcomes, is the lack of control in the gravity feed system. When the patient's head position changes (i.e. when he is looking up or down), the flow rate of this gravity feed system automatically changes. Furthermore, the gravity feed system does not have an easily controlled and reliable adjustment for changes in atmospheric condition.

One mobile infusion system has been described by Dohlman, Doane and Reshni in "Mobile Infusion Pumps for Continuous Delivery of Fluid and Therapeutic Agents to the Eye" which was published in Annals of Ophthal., February, 126, 1971. This paper describes a battery powered device which is worn on the body to pump the artificial tear solution to the eye. However, this device weighs approximately 25 ounces and therefore cannot be conveniently mounted on the frame of a pair of eyeglasses. Additionally, this infusion pump has a high initial cost and some operating cost due to component replacement and battery recharge. In addition, the rate of flow of this mobile infusion system can only be adjusted by removing the infusion pump from the body and adjusting it with the use of a flow meter.

A second mobile infusion system is described in "A New Extracorporeal Tear Duct", published in the Proceedings of A.C.E.M.B., 13:275, 1971, authored by Summers and Doane. This paper reports on a battery powered device, approximately the size of a cigarette pack, for pumping the solution to the eye. The main problems of this device are vibration and wear. This pump, which is a solenoid driven plunger pump, vibrates excessively and some of its parts have a very high wear rate.

A third mobile infusion pump has been developed by Sage Instruments, Inc. of White Plains, N.Y. This Sage Microflow Pump Model 216 operates by displacing the artificial tears contained in a reservoir with a gas which is generated from an electrolytic gel. The main problems with this pump are unreliability, high operating cost, and difficulty of operation. Patients have complained that the pump stops frequently and does not easily start. Also, cost of replacing the gel is high in addition to the operation being very untidy.

U.S. patents to Ness (U.S. Pat. Nos. 3,416,530 and 3,618,604) and to Neefe (U.S. Pat. Nos. 3,710,796 and 3,786,812) all show different ocular inserts for delivering drugs to the eye. However, none of these inserts are activated by the blinking motion of the patient's eye.

SUMMARY OF THE INVENTION

The present invention relates to a blink-activated duct for supplying a solution to the eye of the user which has particular utility in introducing an artificial tear solution for "dry eye" patients. This device consists mainly of a reservoir section for storing the artificial tear solution and a pumping section for introducing this solution to the eye for the patient.

The pump section can consist of either a contact lens or a tube assembly and operates in response to the blinking of the eye of the patient. This blinking action compresses the lens or tube assembly thereby displacing the solution contained therein to the surface of the eye. A partial vacuum is thus created in the pump section which would cause additional solution to be forced from the reservoir into the pump.

This device is vastly superior to any of the mobile infusion systems mentioned above since the patient's body provides the elements which must be built into all of the prior infusion devices. The patient's brain serves as the flow control element, the surface of the eye is the biological sensor which measures some tear dependent biological or biochemical parameter and operates on the control element to alter the tear delivery rate according to the eye's changing needs for lubrication, and the eyelid serves as the source of energy which is under the control of the brain. Since gravity is not used as the main source of power, there is no problem of lack of gravity feed control, e.g. when the patient's head changes position. The present device allows the patient to respond to changes in atmospheric conditions by either increasing or decreasing his/her blink rate as would a normal person. Additionally, there is no problem of replacement or operating costs as in prior infusion systems. Since the flow rate is biologically controlled, there is no adjustment problem as in prior infusion systems.

OBJECTS OF THE INVENTION

It is accordingly an object of the present invention to overcome the defects of the prior art as mentioned above.

Another object of the present invention is to provide a blink-activated duct which is both safe and economical.

A further object of the present invention is to provide blink-activated artificial tears to dry eye patients.

Still another object of the present invention is to provide a blink-activated duct which is activated by the eyelid of the patient.

Yet another object of the present invention is to provide a blink-activated duct which contains a contact lens or elastic tube assembly for introducing a solution to the eye of the patient.

A further object of the present invention is to provide a blink-activated duct which may be conveniently mounted on the frame of a pair of eyeglasses.

BRIEF DESCRIPTION OF THE DRAWING

The above and additional objects and advantages of the present invention will become more apparent by reference to the description of illustrated embodiments in a drawing thereof in which.

DETAILED DESCRIPTION OF A PREFERRED EMBODIMENT

Figure 1:
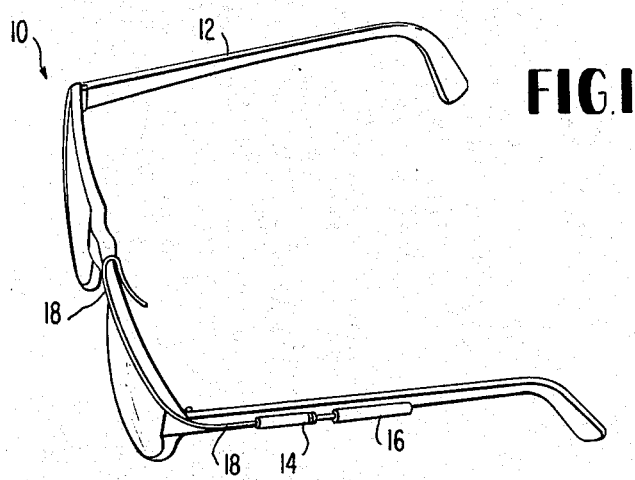
FIG. 1 is a perspective view of a blink-activated duct in accordance with the invention mounted on an eyeglass frame.

FIG. 1 shows the complete device 10 (without the connected pump section) mounted on a standard eyeglass frame 12 which may or may not contain corrective lenses. The entire device is constructed of lightweight durable components so that the system can be easily mounted on the eyeglass frame and does not provide excessive weight.

This device contains a reservoir section 16 which is used to store the artificial tear solution until it is to be introduced into the eye. This reservoir 16 can either be a suitably sized vented container or a throw-away collapsible bag. The collapsible bag is preferable to the container since there is a lower risk of contamination and this bag can be more easily handled by the patient.

This reservoir 16 is connected to a zero backflow check valve 14, which is used to direct the transmission of the solution in the reservoir 16 to the eye of the patient. The components of this check valve 14 will be discussed in detail below. This check valve 14 is in turn connected to a length of tubing 18 which is connected to either a lens connector tubing 36 attached to a contact lens 34 or an elastic tube assembly 38 for introducing the solution to the eye of the patient. While any type of inert tubing can be utilized for the tubing 18, it was found that Teflon tubing was exceptionally suited for this purpose due to its durability, cosmetic properties, chemical inertness, and impermeability to water.

Figure 5:
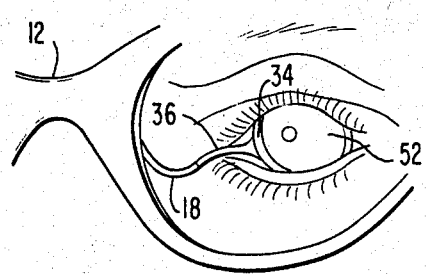
FIG. 5 is a view of the contact lens in place in the eye.

The pump section of this device has been designed to be activated by the blinking action of the patient's eyelids in response to the brain sensing the need for irrigation of the eye. This section consists of a modified hydrophilic contact lens 34 (such as a Bausch & Lomb Softlens) or a small, soft, medical grade tubing assembly 38, preferably formed of silicone rubber, e.g. Silastic. As is shown in FIG. 5, the contact lens 34 is connected to the lens connector 36 which is in turn connected to the tubing 18, is placed directly upon the cornea 52 of the patient.

Figure 4:
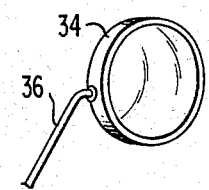
FIG. 4 is a view of a contact lens device in accordance with the present invention.

As shown in FIG. 4, the contact lens 34 is curved similar to the curvature of the eye; however, the radius of the curvature of the contact lens is slightly less than the radius of curvature of the cornea. This enables a slight, thin film of solution to be present between the lens and the cornea in order to ensure a proper oxygen flow to the cornea. This slight difference in curvature also enhances the pumping ability of the lens as will be explained hereinbelow.

Figure 6:
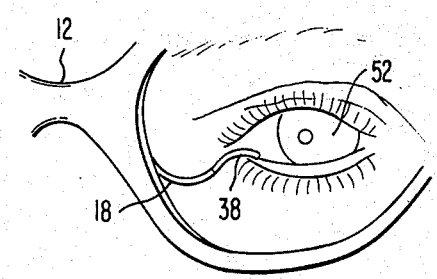
FIG. 6 is a view of the elastic tube in place in the eye.

FIG. 6 shows the Silastic tube assembly 38 connected to the Teflon tube 18 when it is in position for administering the solution to the eye. The tubing assembly 38 is placed near one of the eyelids of the patient or in the cul-de-sac of the conjunctiva of the eye.

Figure 3:
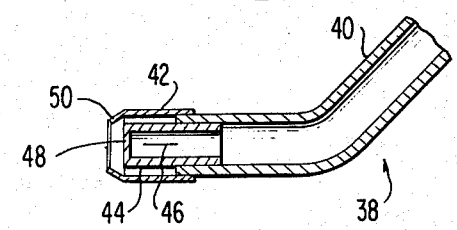
FIG. 3 is a sectional view of an elastic tube assembly in accordance with the present invention.
Figure 2:
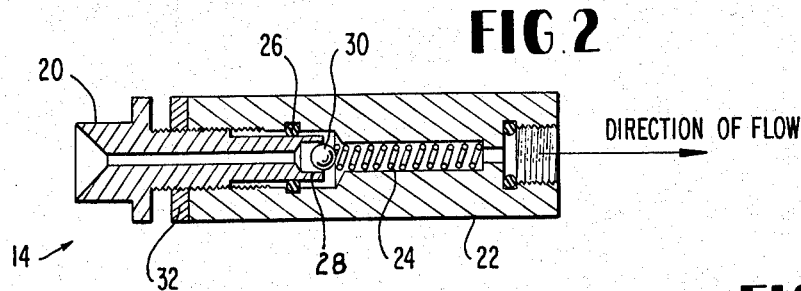
FIG. 2 is a sectional view of a check valve attached to a pump section of a device in accordance with the present invention.

The Silastic tubing assembly 38 is depicted in FIG. 3 and comprises a Silastic tubing 40, a Silastic slit tube 44 having a slit 46, Silastic hypo-tubing 42 encircling the slit tube 44 and a Silastic cover 50. The Silastic slit tube 44 is sealed at 48 in order for the slit to function properly. This tube assembly functions as a final check valve under the control of the eyelid in the same manner as the modified contact lens 34 does. The hypo-tubing 42 provides a protective cover for the slit tube 44 which enhances the performance of the tube assembly 38 by ensuring that the eyelid does not contact the slit 46 enabling the slit to close properly after the ejection of the solution.

As is true with the contact lens embodiment, when the eye requires irrigation, the patient blinks his or her eye and the end of the Silastic tubing assembly 38 is compressed forcing the artificial tear solution out of the slit 46 in the Silastic tube 44. This slit closes by the elastic energy of the Silastic slit tube 44 which restores it to its original shape. The hypo-tubing 42 prevents the eyelid from directly contacting the slit which would inhibit the performance of the assembly. Although the exact configuration of this Silastic tubing assembly 38 has been described in great detail, it can be appreciated that alternate designs by one possessing ordinary skill in the art are possible utilizing different components, without departing from the invention.

To further enhance the performance of this device and to ensure the correct direction of flow of the tear solution, a cylindrical substantially zero back-flow sensitive check valve 14, containing a valve body 22 and a seat assembly 20 is provided. This seat assembly 20 is directly connected to the reservoir 16 in any conventional manner in order to help provide a smooth flow of solution when required. The valve body 22 contains a ball valve 30, cooperatively engaged with a standard compression spring 24, which is seated against a silicone rubber seat 28. Two O-ring seals 26 are provided to maintain a closed system. If a partial vacuum is created in the pump section, the ball 30 becomes unseated from the silicone rubber seat 28 and additional solution can then travel from the reservoir into the tubing 18 and thence to the lens tubing 36 or the Silastic tubing assembly 38. An adjustable stop nut 32 is provided around the seat assembly 20 to adjust the spring 24 until the correct spring tension can be determined.

The above-described blink-activated tear duct can be operated in the following manner. When the brain senses the need for lubrication in the eye, an involuntary muscle contraction allows the patient to blink his or her eye thus compressing the contact lens 34 or the Silastic tube assembly 38 with the eyelids, displacing the tear solution from the compressed section. Since the radius of curvature of the contact lens 34 is slightly smaller than that of the cornea of the eye, the lens "sits up" from the surface of the cornea and the lens thereby acts as an effective pump to allow the solution which is contained in the lens connector tubing 36 to be introduced to the cornea. Similarly, if the Silastic tubing assembly 38 is used, the compressing of the eyelids allows this assembly to also act as a pump in the same general way.

When the upper eyelid retracts, the elastic energy of the compressed component restores that component to its original shape and spreads artifical tears over the eye. When the compressed component is restoring, a partial temporary vacuum is created within the component and tubing and this reduced pressure draws more tear solution into the elastic component from the tubing 18, the zero backflow check valve 14 and the reservoir 16. Therefore, it can be seen that the artificial tear flow is controlled not by any mechanical device but by the person's brain. The use of only a few simple components thus ensures that the cost of operation is minimal. When the reservoir section 16 has dispensed all of the solution contained therein, additional solution can be introduced by either replacing the collapsible bag, or if a vented container has been used as the reservoir, by simply introducing the solution directly into the container.

While this device has been described with particular reference to the introduction of an artificial tear solution, it should not be construed to be so limited and may be utilized with many other solutions. It will be obvious to those skilled in the art that various changes may be made without departing from the scope of the invention and the invention is not to be construed as limited to what is shown in the drawings and described in the specification.

What is claimed is:

1. An eyelid-actuated duct for supplying a beneficial solution to the eye of the user comprising:
   reservoir means for storing the solution;
   pump means for introducing the solution to the eye of the user and for drawing additional solution from said reservoir, said pump means including a compressible and recoverable elastic component for location in cooperative engagement with the eyelid of the user;
   whereby when the upper eyelid of the user exerts pressure upon and compresses said elastic component the solution contained in said pump means is dispersed over the eye of the user, and when said elastic component recovers its uncompressed shape a partial vacuum is created to draw additional solution from said reservoir.

2. An eyelid-actuated duct according to claim 1 further including a check valve means connected between said pump means and said reservoir means for controlling the direction of flow of the solution.

3. An eyelid-actuated duct according to claim 1 further including an eyeglass frame wherein said reservoir means is attached to said eyeglass frame.

4. An eyelid-actuated duct according to claim 1 wherein said pump means is a hydrophilic contact lens having a connector tubing attached thereto.

5. An eyelid-actuated duct according to claim 1 wherein said pump means comprises:
   a connector tube;
   a slit tube connected to said connector tube;
   hypo-tubing surrounding said slit tube; and
   a hypo-tubing cover surrounding said slit tube.

6. An eyelid-actuated tear duct according to claim 5 wherein said connector tube, said slit tube and said hypo-tubing are constructed of Silicone rubber.

7. An eyelid-actuated duct according to claim 1 wherein said reservoir means is a removable collapsible bag.

8. An eyelid-actuated duct according to claim 1 wherein said reservoir means is a vented container.

* * * * *